United States Patent [19]

Fluckiger et al.

[11] Patent Number: 5,171,274
[45] Date of Patent: Dec. 15, 1992

[54] IMPLANT FOR REPLACING A LIGAMENT OR TENDON

[75] Inventors: Hans Fluckiger, Oetwil am See; Stefan Freudiger, Bremgarten; Rudolf Koch, Berlingen, all of Switzerland

[73] Assignees: Sulzer Brothers Limited, Winterthur; Protek AG, Berne, both of Switzerland

[21] Appl. No.: 751,111

[22] Filed: Aug. 28, 1991

[30] Foreign Application Priority Data

Sep. 7, 1990 [CH] Switzerland ............ 2910/90

[51] Int. Cl.$^5$ .............................. A61F 2/08
[52] U.S. Cl. ..................... 623/13; 623/11; 623/20
[58] Field of Search .................. 623/11–13, 623/20

[56] References Cited

U.S. PATENT DOCUMENTS

| | | | |
|---|---|---|---|
| 3,176,316 | 4/1965 | Bodell | 623/13 |
| 4,149,277 | 4/1979 | Bokros | 623/13 |
| 4,584,722 | 4/1986 | Levy et al. | 623/13 |
| 4,795,466 | 1/1989 | Stuhmer et al. | 623/13 |
| 4,883,486 | 11/1989 | Kapadia et al. | 623/13 |

FOREIGN PATENT DOCUMENTS 0145492 6/1985 European Pat. Off. .
2395012 1/1979 France .

Primary Examiner—Ronald Frinks
Attorney, Agent, or Firm—Kenyon & Kenyon

[57] ABSTRACT

A prosthetic ligament implant is sheathed at one end in the sock in order to facilitate pulling of the implant through a hole drilled in a bone. The sock is provided with a separable proximal portion which does not envelope the implant and which can be cut off after pulling of the implant through the hole in the bone. With removal of the proximal portion, the remaining textile structure of the sock becomes asunder so that the sock can be readily pulled off from the end of the implant.

8 Claims, 2 Drawing Sheets

IMPLANT FOR REPLACING A LIGAMENT OR TENDON

This invention relates to an implant for replacing a ligament or tendon.

Heretofore, various types of implants have been known for replacing ligaments and tendons in the human body. For example, U.S. Pat. No. 4,883,486 describes a prosthetic ligament which is constructed of an elongated tubular sheath of yarn with a core of unwoven non-braided strands which is anchored to the sheath with a stitching of multi-filament synthetic thread. Once implanted, the sheath remains part of the prosthetic ligament. Similar prosthetic ligaments or tendons are described in French Patent No. 2,395,012 and U.S. Pat. No. 4,584,722.

Still other types of prosthetic tendons have been known, such as described in U.S. Pat. No. 3,176,316, which employ a solid or semi-solid flexible shaft within an outer shell or sheath of woven material or as described in European Patent Application No. 0 145 492 which employ a core of filaments within a braided sleeve.

If implants of the above type, particularly, as shown in French Patent No. 2,395,012, have to be passed through holes drilled in a bone, for example, as replacements for crucial ligaments in a femur and/or tibia, difficulties frequently arise in doing so, particularly, if the end of the implant which has to be pulled through the bone is loosened into individual strands or threads or is made as an anchoring eye.

Accordingly, it is an object of the invention to facilitate the threading of an implant through a bone to act as a prosthetic ligament or tendon.

It is another object of the invention to facilitate s implantation of a prosthetic ligament or tendon in a knee joint to replace a crucial ligament.

Briefly, the invention provides an implant which is comprised of a plurality of longitudinal parallel threads with a textile sock for insertion of the implant through a hole in a bone. In accordance with the invention, the textile sock has an intermediate portion extending concentrically about the threads of the implant, a distal portion extending coaxially from the immediate portion and the implant for passage through a bore in a bone and a proximal portion extending from the intermediate portion laterally of the implant, i.e. without enveloping the longitudinal threads of the implant.

With this construction, during implantation, the distal end of the sock can be threaded into a hole drilled in a bone and pulled through the hole. In doing so, the sock sheaths the longitudinally parallel threads of the implant only until after being pulled through. After the proximal portion of the sock which does not sheath any threads "emerges" again at the end of the hole drilled in the bone, this proximal end of the sock is cut off. Thus, the textile pattern of the sock partially loosens or, for example, in the case of being knitted, may be unraveled. The remainder of the sock may then be removed in a simple way from the longitudinal threads of the implant which has been pulled through the bone.

Threading in and pulling through of the sock and implant may be facilitated if the threads of the implant are of different length within the intermediate portion of the sock in order to form a conically tapered shape.

It is proved advantageous if the sock consists of a braid since by setting the braiding angle, i.e. the angle which the braided threads make with the longitudinal axis of the braid, the compactness and stiffness of the braided end of the implant may be varied to some extent. First, the diameter of the braided strands of thread can be thereby reduced and, secondly, the "sticking" of the sock onto the end of the longitudinal threads is guaranteed by friction.

These and other objects and advantages of the invention will become more apparent from the following detailed description taken in conjunction with the accompanying drawings wherein.

Figure 1:
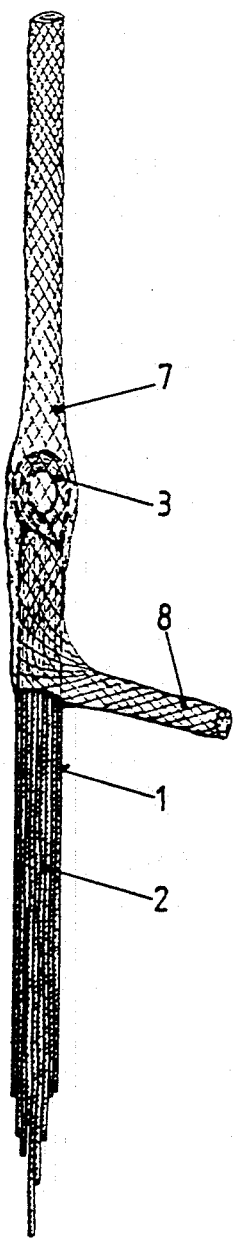
FIG. 1 illustrates an implant having a sock thereon in accordance with the invention.

Referring to FIG. 1, an implant 1 which is employed as a replacement for a crucial ligament consists, at least partially, of a plurality of longitudinal parallel monofilament threads or strands of threads 2. The individual strands of thread 2 may be reinforced in their strength by braiding, twisting or warping. In addition, one end of the implant 1 is made as an eye for passage of an anchoring screw therethrough as is known.

Figure 2:
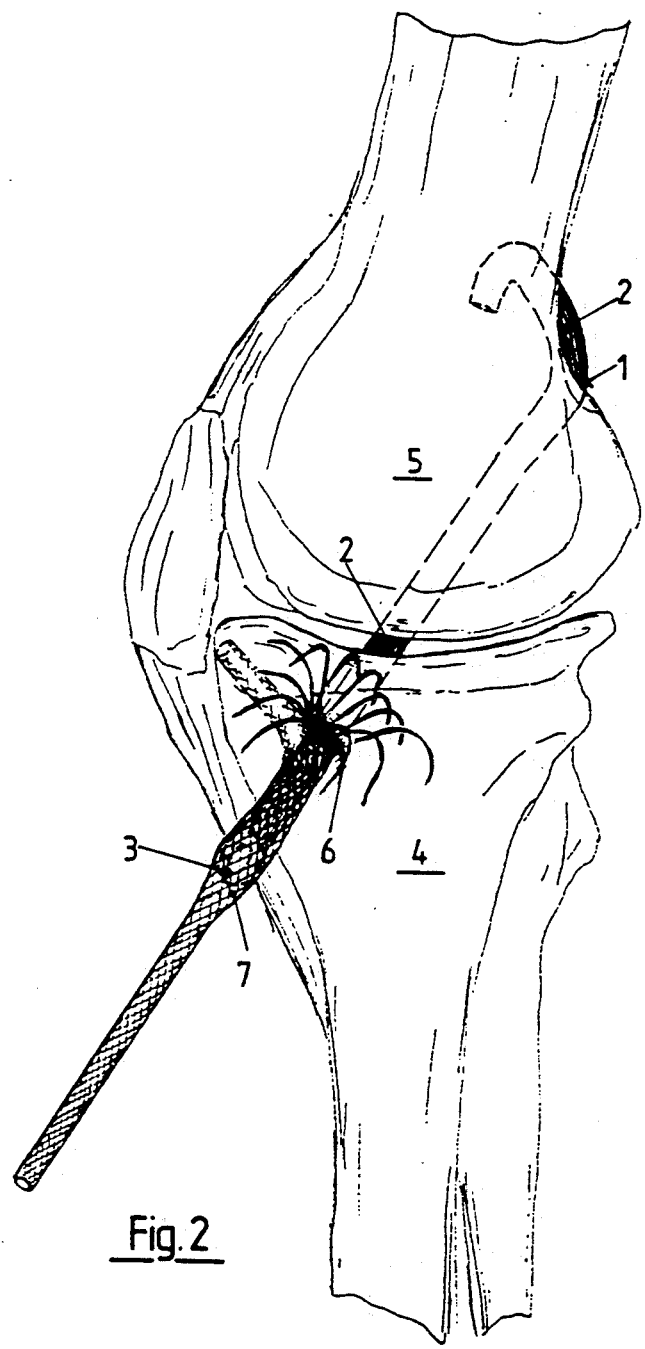
FIG. 2 illustrates the position of the implant and sock after threading through a femur and tibia in accordance With the invention.

Referring to FIG. 2, the implant 1 is constructed so as to be passed through a tibia 4 and femur 5 to replace a crucial ligament. To this end, the femur 5 and tibia 4 are provided with suitable holes 6 to permit passage of the implant therethrough.

As shown in FIGS. 1 and 2, a textile sock 7 is disposed over the end of the implant 1 which is to be passed through the holes 6 in the femur 5 and tibia 4. This textile sock 7 is of braided construction and has an intermediate portion extending concentrically about the threads 2 of the implant 1, a distal portion which extends coaxially from the intermediate portion and from the implant 1 for passage through a hole 6 in the respective bones 4, 5 and a proximal portion 8 which extends from the intermediate portion laterally of the implant 1. As indicated in FIG. 1, the proximal portion 8 of the sock 7 does not envelope any of the threads 2 of the implant 1. Accordingly, this proximal portion 8 may have a sharply reduced diameter.

Referring to FIG. 2, with the sock 7 disposed about the eye-containing end of the implant 1, the distal portion of the sock 7 is passed through the holes 6 in the femur 5 and tibia 4 with the implant 1 being pulled therewith. After being pulled through the bone or bones 5, 4, the proximal portion 8 of the sock 7 is severed from the remainder of the sock 7. If the sock 7 is braided, the individual "prestressed" threads of the braid fan out like the calyx of a flower. The remainder of the sock 7 can then, if necessary, after further loosening of its braid by the operating surgeon, be pulled off the end of the implant 1. In the event that the sock 7 is formed of a single endless thread, the remainder of the sock 7 can be simply unraveled after removal of the proximal portion 8.

Figure 3:
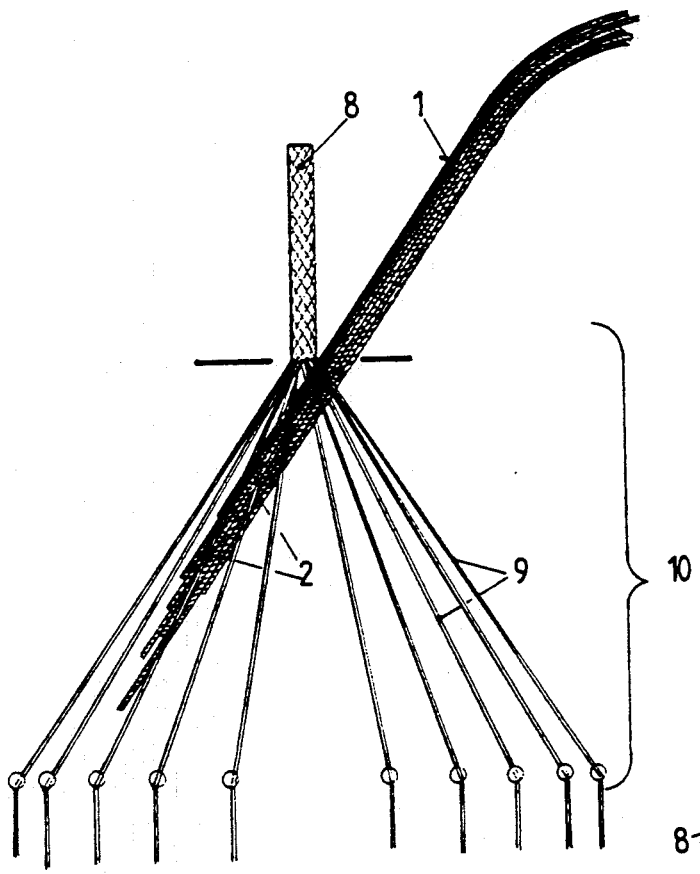
FIG. 3 illustrates a manner in which the sock is braided about the longitudinal threads of the implant in accordance with the invention.

Referring to FIG. 3 in order to form a sock 7 over the implant 1, use may be made of a braiding machine having a braiding region 10 in which individual threads 9 of the sock 7 can be braided over the threads 2 of the implant 1. In this respect, the proximal end 8 of the sock 7 is first braided from the individual threads 9 which may be made as monofilaments or multifilaments. When this proximal portion 8 has reached the required length, the end of the implant 1 to be sheath is introduced into the braiding region 10 of the machine and braiding is continued until the sock 7 completely encloses the strands of thread 2 of the implant 1, or, if necessary, is extended beyond the threads 2.

Figure 4:
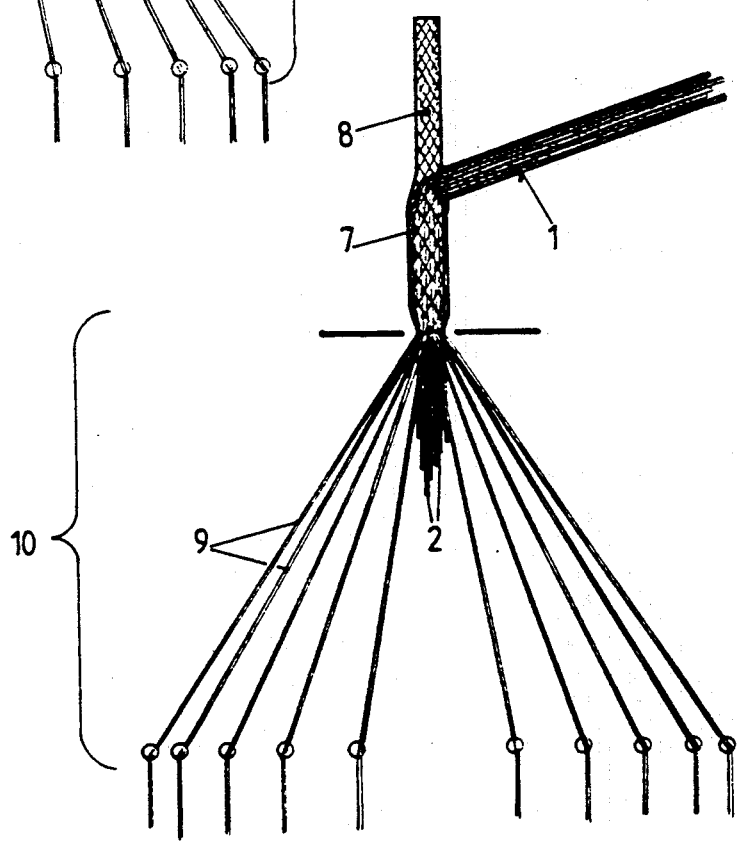
FIG. 4 diagrammatically illustrates the braiding of an intermediate portion of the sock about the longitudinal threads of an implant in accordance with the invention.

As indicated in FIG. 4, during braiding of the threads 9 about the implant 1, the intermediate portion of the sock 7 is formed completely about the threads 2 of the implant. At this time, the outer diameter of the sock 7 is increased relative to the diameter of the proximal portion 8.

In contrast to the implant of FIGS. 1 and 2, the end of the implant shown in FIGS. 3 and 4 may omit an eye but may have threads 2 of unequal length such that the intermediate portion of the sock 7 obtains a conically tapered shape. Thus, threading into and pulling through a hole 6 drilled in a bone 4, 5 are facilitated.

The invention thus provides a sock which facilitates insertion of an implant which can be used to replace a ligament or tendon and which can be subsequently removed from the implant in a simple manner.

What is claimed is:

1. In combination
   an implant comprising a plurality of longitudinal parallel threads, at least a portion of each of said threads being free to move independently of each of the other threads; and
   a textile sock for holding said threads next to one another during insertion of the implant, said sock having an intermediate portion extending concentrically about said threads, a distal portion extending coaxially from said intermediate portion and said implant for passage through a bore in a bone, and a proximal portion extending from said intermediate portion laterally of said implant.

2. The combination as set forth in claim 1 wherein said threads are of different length within said intermediate portion of said sock to form a conically tapered shape.

3. The combination as set forth in claim 1 wherein said sock is braided.

4. The combination as set forth in claim 1 wherein said threads form an eye within said intermediate portion of said sock.

5. The combination as set forth in claim 1 wherein at least some of said threads are reinforced by at least one of braiding, twisting and warping.

6. The combination as set forth in claim 1 wherein said distal portion of said sock is made of a plurality of individual threads.

7. In combination
   an implant comprising a plurality of longitudinal parallel threads; and
   a textile sock having an intermediate portion extending concentrically about said threads, said threads being of different length within said intermediate portion of said sock to form a conically tapered shape, a distal portion extending coaxially from said intermediate portion and said implant for passage through a bore in a bone, and a proximal portion extending from said intermediate portion laterally of said implant.

8. In combination
   an implant comprising a plurality of longitudinal parallel threads; and
   a textile sock having an intermediate portion extending concentrically about said threads, said threads forming an eye in said intermediate portion of said sock, a distal portion extending coaxially from said intermediate portion and said implant for passage through a bore in a bone, and a proximal portion extending from said intermediate portion laterally of said implant.

* * * * *